(12) United States Patent
Jurgelas

(10) Patent No.: US 9,414,969 B2
(45) Date of Patent: Aug. 16, 2016

(54) CAST COVERS

(71) Applicant: Maureen Jurgelas, Marietta, GA (US)

(72) Inventor: Maureen Jurgelas, Marietta, GA (US)

( * ) Notice: Subject to any disclaimer, the term of this patent is extended or adjusted under 35 U.S.C. 154(b) by 0 days.

(21) Appl. No.: 14/603,348

(22) Filed: Jan. 22, 2015

(65) Prior Publication Data

US 2015/0202538 A1    Jul. 23, 2015

Related U.S. Application Data

(60) Provisional application No. 61/930,325, filed on Jan. 22, 2014.

(51) Int. Cl.
| | | |
|---|---|---|
| A63H 33/00 | (2006.01) |
| A61F 13/10 | (2006.01) |
| A61F 13/06 | (2006.01) |
| A61F 13/00 | (2006.01) |

(52) U.S. Cl.
CPC ............... *A61F 13/10* (2013.01); *A61F 13/06* (2013.01); *A61F 2013/00153* (2013.01)

(58) Field of Classification Search
USPC .............. 446/26, 71, 72, 73, 75, 77; 2/16, 22; 602/3
See application file for complete search history.

(56) References Cited

U.S. PATENT DOCUMENTS

| | | | | | |
|---|---|---|---|---|---|
| 4,661,072 | A | * | 4/1987 | White | 434/260 |
| D343,903 | S | * | 2/1994 | Perteet | D24/206 |
| 5,477,560 | A | * | 12/1995 | Shope | 2/49.1 |
| 5,504,944 | A | * | 4/1996 | Bromer et al. | 2/269 |
| D395,087 | S | * | 6/1998 | Devries | D24/190 |
| 5,978,962 | A | * | 11/1999 | Hamowy | 2/16 |
| 7,237,347 | B2 | * | 7/2007 | Tobias | 36/112 |
| 8,043,240 | B2 | * | 10/2011 | Piatek | 602/3 |
| 8,062,087 | B1 | * | 11/2011 | Davis et al. | 446/26 |
| 8,430,829 | B1 | * | 4/2013 | Marchetti | 602/3 |
| 8,905,810 | B2 | * | 12/2014 | Muccini et al. | 446/26 |
| 2007/0015434 | A1 | * | 1/2007 | Preece | 446/328 |
| 2008/0076318 | A1 | * | 3/2008 | Diep | 446/26 |
| 2008/0096457 | A1 | * | 4/2008 | Urias | 446/26 |
| 2008/0208094 | A1 | * | 8/2008 | Gaylord | 602/23 |
| 2009/0188445 | A1 | * | 7/2009 | Jacobsen | 119/850 |
| 2011/0282254 | A1 | * | 11/2011 | Gadlage | 602/3 |
| 2012/0329357 | A1 | * | 12/2012 | Brodess | 446/26 |
| 2013/0096474 | A1 | * | 4/2013 | Sager | 602/3 |
| 2014/0005582 | A1 | * | 1/2014 | Dickison et al. | 602/3 |

* cited by examiner

*Primary Examiner* — Kurt Fernstrom
(74) *Attorney, Agent, or Firm* — Incorporating Innovation LLC; Charlena Thorpe, Esq.

(57) ABSTRACT

Implementations of ornamental cast covers are provided. In some implementations, the ornamental cast cover comprises a puppet having at least one set of appendages and one or more elastics bands each connecting a portion of the puppet on one side of the puppet to a portion of the puppet on the other side of the puppet. In some implementations, the ornamental cast cover comprises an elongated tubular leg portion having an opening through the leg portion and a foot portion having an opening through the foot portion and a flap. The flap may be detached from a portion of the cast cover to create a larger opening to insert an appendage having a cast or brace thereon. In some implementations, the leg portion and foot portion are configured to receive a cast or brace therein. In some implementations, the ornamental cast cover comprises an elongated tubular portion having a first end and a second end and a thumb strap extending from the elongated tubular portion.

7 Claims, 3 Drawing Sheets

CAST COVERS

CROSS REFERENCE TO RELATED APPLICATION

This application claims the benefit of U.S. patent application Ser. No. 61/930,325, which was filed on Jan. 22, 2014, and is incorporated herein by reference in its entirety.

TECHNICAL FIELD

This disclosure relates to implementations of ornamental cast covers.

BACKGROUND

Cast covers may be designed to embellish a cast. Typically, these cast covers are designed to snugly fit a cast for aesthetics. However, these decorative cast covers can be difficult to place over a cast. Furthermore, existing decorative cast covers cannot be used for any other purpose other than to cover a cast.

DETAILED DESCRIPTION

Implementations of ornamental cast covers are provided. In some implementations, the ornamental cast cover comprises a puppet having at least one set of appendages and one or more elastics bands each connecting a portion of the puppet on one side of the puppet to a portion of the puppet on the other side of the puppet. In some implementations, the puppet is a stuffed toy having a body and at least one set of appendages.

In some implementations, the ornamental cast cover comprises an elongated tubular leg portion having an opening through the leg portion and a first flap and a foot portion having an opening through the foot portion and a second flap. The flaps may be detached from the remainder of the cast cover to create a larger opening to insert an appendage having a cast or brace thereon. In some implementations, the leg portion and foot portion are configured to receive a cast or brace therein. In some implementations, the foot portion further comprises one or more non-slip pads. In some implementations, the leg portion does not include a flap.

In some implementations, the ornamental cast cover comprises an elongated tubular portion having a first end and a second end and a thumb strap extending from the elongated tubular portion. The first end includes an opening configured to receive a cast or brace therein. The second end includes a second and third opening. In some implementations, the second opening may be configured to receive one or more fingers of a wearer. In some implementations, the third opening may be configured to receive the thumb of the wearer. In some implementations, the thumb strap extends from the cast cover on a side opposite the third opening. In some implementations, the distal end of the thumb strap may include fastening means thereon for securing the distal end of the thumb strap to the cast cover.

Figure 1A:
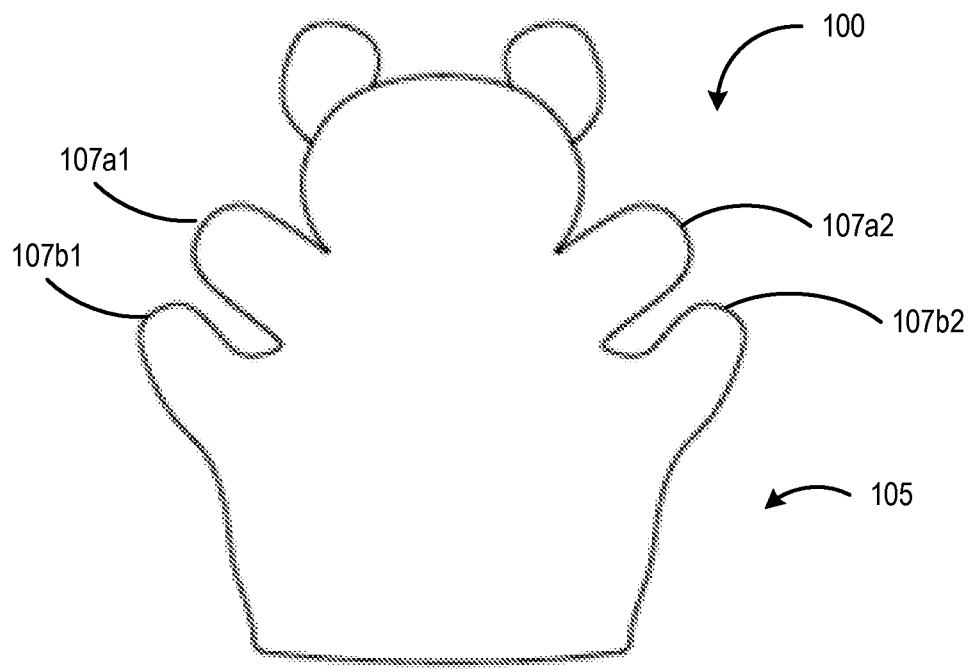
FIGS. 1A and 1B illustrate an implementation of an example ornamental cast cover according to the present disclosure.
Figure 1B:
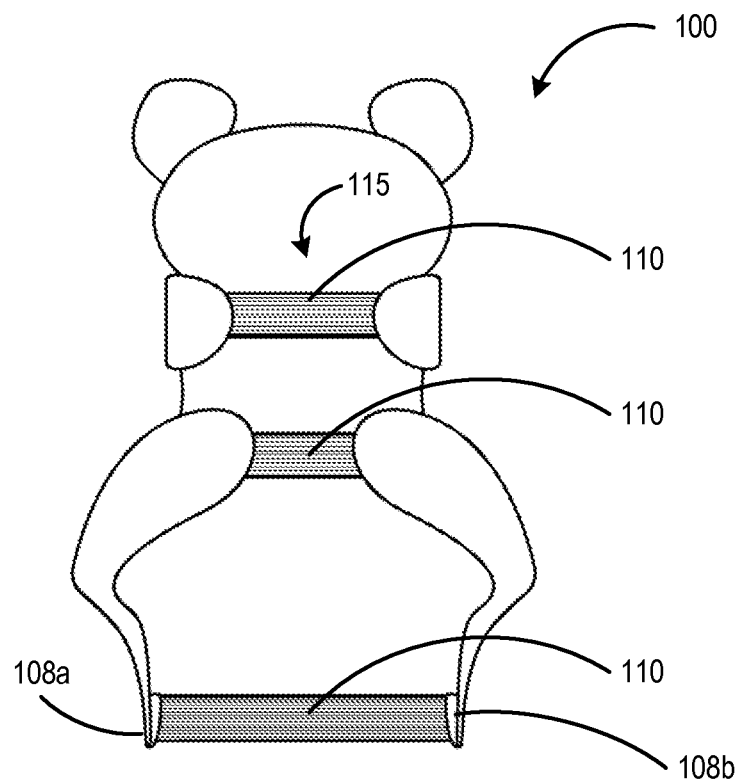

FIGS. 1A and 1B illustrate an implementation of an example ornamental cast cover 100 according to the present disclosure. In some implementations, the cast cover 100 comprising a puppet 105, wherein the puppet 105 has at least one set of appendages (e.g., 107a1, 107a2 and/or 107b1, 107b2). In some implementations, the appendages of a set are located on opposite sides of the puppet 105.

As shown in FIG. 1B, the cast cover 100 further comprises one or more elastics bands 100 each connecting a portion of the puppet 105 on one side of the puppet 105 to a portion of the puppet 105 on the other side of the puppet 105.

In some implementations, an elastic band may connect a first appendage (e.g., 107a1 and/or 107b1) on a first side of the puppet to a second appendage (e.g., 107a2 and/or 107b2, respectively) on a second side of the puppet 105.

In some implementations, an elastic band may connect a portion (e.g., portion 108a) of the puppet 105 on a first side to a portion (e.g., portion 108b) of the puppet 105 on a second side.

In some implementations, an elastic band may connect a bottom portion (e.g., portion 108a) of the puppet 105 on one side of the puppet 105 to a bottom portion (e.g., portion 108a) of the puppet 105 on the other side of the puppet 105.

In some implementations, an elastic band may connect a top, middle, and bottom portion (or any combination of the foregoing) of the puppet 105 on one side of the puppet 105 to a top, middle, and bottom portion (or any combination of the foregoing), respectively, of the puppet 105 on the other side of the puppet 105. In some implementations, an elastic band may connect any other portion of the puppet 105 on one side of the puppet 105 to any other portion of the puppet 105 on the other side of the puppet 105.

By connecting one or more elastics bands 100 to connect one or more portions of the puppet 105 on one side of the puppet 105 to one or more portions of the puppet 105 on the other side of the puppet 105, one or more closed loops 115 are formed to receive a cast or brace therein. Accordingly, the elastic bands 110 may be used to secure the ornamental cast cover 100 on a cast or brace.

In some implementations, the elastic bands 110 are sewn or removably attached to the puppet 105. In some implementations, the elastic bands 110 includes fastening means such as snaps, buttons, hook and loop fasteners (e.g., Velcro®), magnets or other reclosable fasteners or any other attachment or fastening technology existing or developed in the future to secure the elastic bands 110 to the cast cover 100.

In some implementations, the closed loops 115 of the cast cover 100 may be configured to receive a hand and/or wrist cast. In some implementations, the closed loops 115 of the cast cover 100 may be configured to receive a hand and/or wrist brace.

In some implementations, the puppet 105 may be a stuffed toy having a body and appendages (e.g., hands and/or legs).

To use the ornamental cast cover 100, a cast or brace is inserted into a one or more closed loops 115 of the cast cover 100 and then the cast cover 100 is positioned in the desired position on the cast or brace.

In some implementations, after a cast or brace is no longer needed, the elastic bands 110 of the ornamental cast cover may be removed or cut to use the puppet or toy as a puppet or toy.

In some implementations, the ornamental cast cover 100 may be used in conjunction with another cast cover. For example, in some implementations, the ornamental cast cover 100 can be placed on top of another cast cover.

Figure 2A:
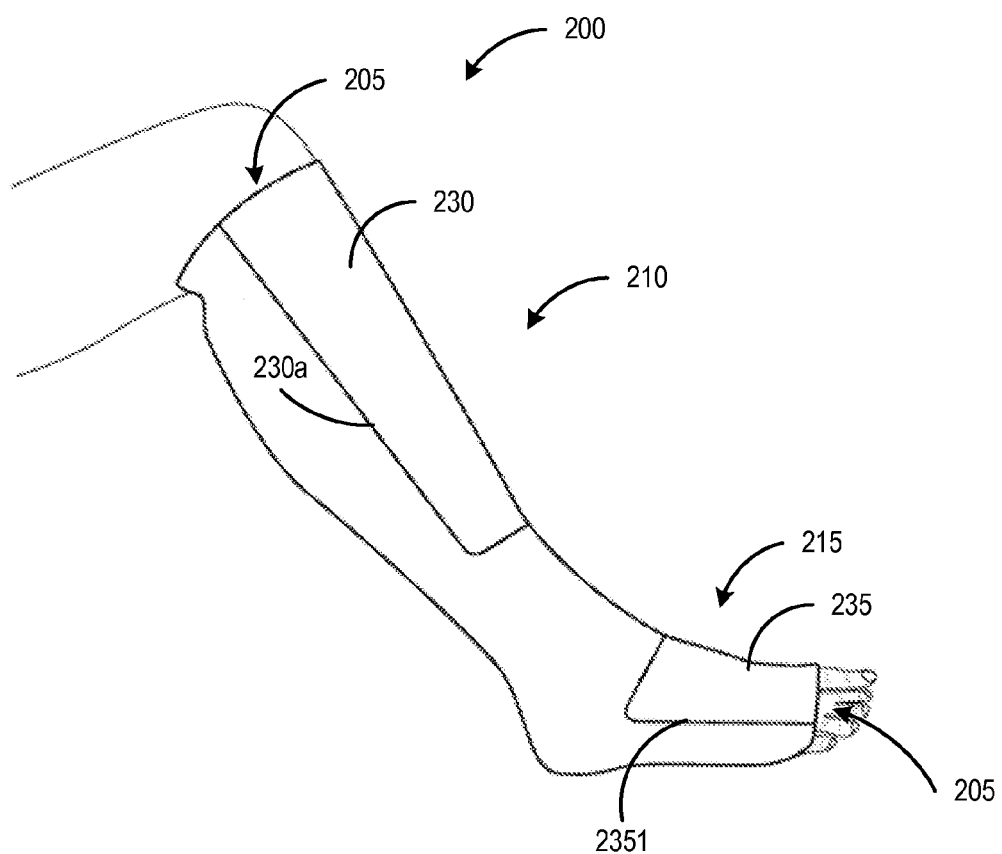
FIG. 2A illustrates another implementation of an example ornamental cast cover according to the present disclosure.

FIG. 2A illustrates another implementation of an example ornamental cast cover 200 according to the present disclosure.

In some implementations, the ornamental cast cover 200 comprising an elongated tubular leg portion 210 having an opening through the leg portion 210 and a flap 230 and a foot portion 215 having an opening through the foot portion and a flap 235. The leg portion 210 and foot portion are configured to receive a cast or brace therein. In some implementations, the foot portion 215 further comprises one or more non-slip pads (not shown) on the bottom of the foot portion. In some implementations, the cast cover 200 may further comprise elastic located about the openings 205 of the cast cover 200. The elastic may help secure the ornamental cast cover 200 on a cast or brace.

In some implementations, an edge 230a of the flap 230 of the leg portion 210 may be attachable to/detachable from a portion of the leg portion 210 by any fastening means such as snaps, buttons, hook and loop fasteners (e.g., Velcro®), magnets or other reclosable fasteners or any other attachment or fastening technology existing or developed in the future. The flap 230 may be detached from a portion of the leg portion 210 to create a larger opening to insert an appendage having a cast or brace thereon.

In some implementations, an edge 235a of the flap 235 of the foot portion 215 may be attachable to/detachable from a portion of the foot portion 215 by any fastening means such as snaps, buttons, hook and loop fasteners (e.g., Velcro®), magnets or other reclosable fasteners or any other attachment or fastening technology existing or developed in the future. In some implementations, the edge 235a may extend to a portion on the bottom of the foot portion 215. In some implementations, the edge 235a may extend to a side of the foot portion 215. In some implementations, the edge 235a may extend to any other portion of the foot portion 215. In some implementations, the flap 235 may be detached from a portion of the foot portion 215 to create a larger opening to insert an appendage having a cast or brace thereon.

In some implementations, the non-slip pads may prevent a user from slipping when walking on some surfaces. In some implementations, the non-slip pads are made from a tacky material.

In some implementations, the cast cover 200 may not include a foot portion 215. In some implementations, the cast cover 200 may not include a leg portion 210.

Figure 2B:
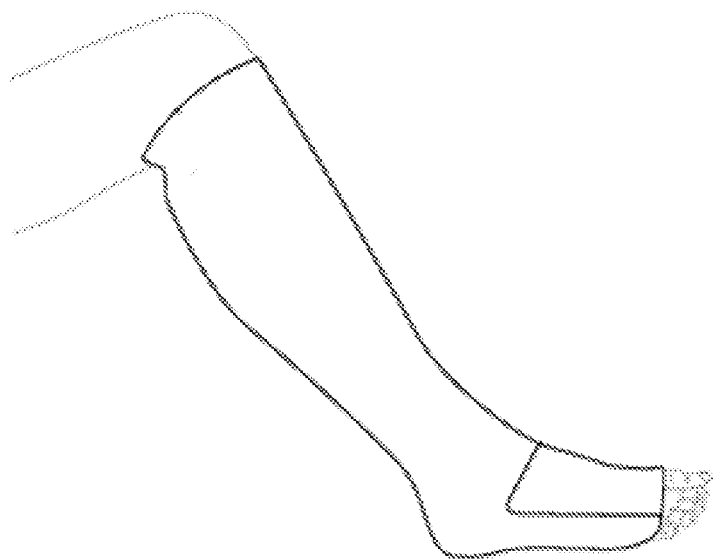
FIG. 2B illustrates another implementation of an example ornamental cast cover according to the present disclosure.

In some implementations, the leg portion 210 of the cast cover 200 does not include a flap as shown in FIG. 2B.

In some implementations, the cast cover 200 may be worn over a portion of a brace. In some implementations, the cast cover 200 may have a decorative pattern thereon. In some implementations, the cast cover 200 may have a decorative print thereon. In some implementations, the cast cover 200 may be a solid color or multi-colored.

In some implementations, to use the ornamental cast cover 200, the flap 230 of the leg portion 210 and the flap 235 of the foot portion 215 may be initially opened. The user may then insert a cast or brace into the opening of the cast cover 200 and then the cast cover 200 is positioned in the desired position on the cast or brace. The user may then fasten the flaps 230, 235 closed.

Figure 3A:
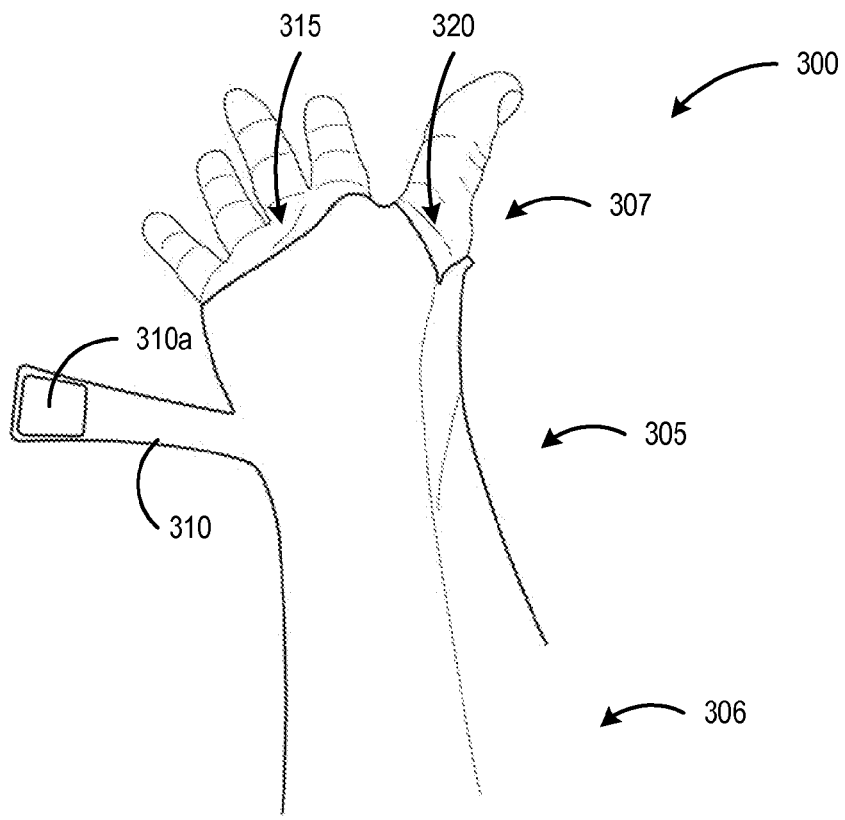
FIGS. 3A and 3B illustrate another implementation of an example ornamental cast cover according to the present disclosure.
Figure 3B:
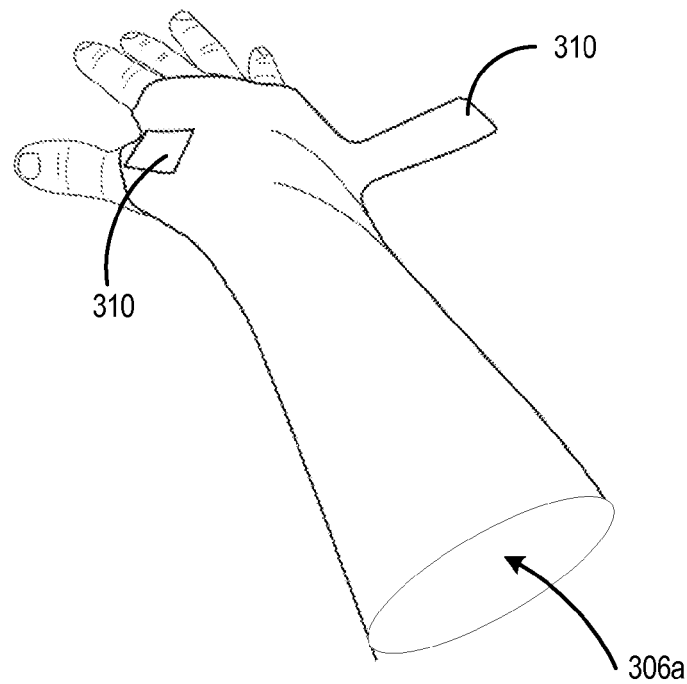

FIGS. 3A and 3B illustrate another implementation of an example ornamental cast cover 300 according to the present disclosure.

As shown in FIGS. 3A and 3B, in some implementations, the ornamental cast cover 300 comprises an elongated tubular portion 305 having a first end 306 and a second end 307 and a thumb strap 310 extending from the elongated tubular portion 305. The first end 306 includes an opening 306a configured to receive a cast or brace therein. The second end 307 includes two separate openings 315, 320. In some implementations, the cast cover 300 may further comprise elastic located about the openings 306a, 315, 320 of the cast cover 200. The elastic may help secure the ornamental cast cover 300 on a cast or brace.

In some implementations, the opening 315 may be configured to receive one or more fingers of a wearer, as shown in FIG. 3A. In some implementations, the opening 320 may be configured to receive the thumb of the wearer, as shown in FIG. 3A.

In some implementations, the thumb strap 310 extends from the cast cover 300 on a side opposite the opening 320. In some implementations, the distal end 310a of the thumb strap 310 may include fastening means thereon for securing the distal end of the thumb strap to cast cover 300. In some implementations, the distal end 310a of the thumb strap 310 may be secured to a portion (e.g., portion 330) of the cast cover 300 using fastening means such as snaps, buttons, hook and loop fasteners (e.g., Velcro®), magnets or other reclosable fasteners or any other attachment or fastening technology existing or developed in the future.

In some implementations, the distal end 310a of the thumb strap 310 may be secured to a portion (e.g., portion 330) of the cast cover 300 located adjacent the thumb opening 315.

In some implementations, the cast cover 300 may have a decorative pattern thereon. In some implementations, the cast cover 300 may have a decorative print thereon. In some implementations, the cast cover 300 may be a solid color or multi-colored. In some implementations, elastic may be located about the openings of the first end 306 and second end 307 of the cast cover. The elastic may help secure the ornamental cast cover in place.

To use the ornamental cast cover 300, the cast or brace is inserted into the opening 306a of the first end 306 of the sleeve 305 and then the cast cover 300 may be pulled over the cast or brace, and positioned so that the user's fingers extend through opening 315 and the user's thumb extends through opening 320 of the sleeve 305. The thumb strap 310 may then be pulled across the palm of the hand and fastened to a portion (e.g., portion 330) of the cast cover 300 located near the thumb opening 320.

In some implementations, the thumb strap 310 may be pulled across the palm of the hand and attached to a portion of the cast cover 300 located between the thumb and forefinger. In some implementations, the thumb strap 310 may be attached to a portion of the cast cover 300 located on the top side (i.e., the side opposite the palm) of the hand. In some implementations, the thumb strap 310 provides a means to adjust the fit of the cast cover 300.

In some implementations, the ornamental cast covers 100, 200, 300 or portions thereof may be manufactured from a textile material. In some implementations, the ornamental cast covers 100, 200, 300 or portions thereof may be manufactured from rayon, spandex, polyester, nylon, blends thereof, or combinations thereof. In some implementations, the ornamental cast covers 100, 200, 300 or portions thereof may be manufactured from a material comprised of 20% spandex and 80% nylon. In some implementations, the ornamental cast covers 100, 200, 300 or portions thereof may be manufactured from machine washable materials. In some implementations, the ornamental cast covers 100, 200, 300 or portions thereof may be manufactured from a breathable material. In some implementations, the ornamental cast covers 100, 200, 300 or portions thereof may be manufactured from a water proof material or a non-permeable material. In some implementations, the ornamental cast covers 100, 200, 300 or portions thereof may be manufactured from any synthetic, semi-synthetic, natural fiber, or combination thereof, material. In some implementations, the ornamental cast cover 100, 200, 300 or portions thereof may be manufactured from any suitable material.

Reference throughout this specification to "an embodiment" or "implementation" or words of similar import means that a particular described feature, structure, or characteristic is included in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations are depicted in the drawings in a particular order, this should not be understood as requiring that such operations be performed in the particular order shown or in sequential order, or that all illustrated operations be performed, to achieve desirable results.

The invention claimed is:

1. A cast cover comprising:
    a puppet having a body portion and at least one set of appendages wherein the body portion and the appendages comprise opening for receiving a user's hand and fingers respectively to allow for dual use of the puppet as a cast cover and a puppet; and
    one or more elastics bands wherein for each elastic band a first end of the elastic band is attached to a portion of the puppet on one side of the puppet and a second end of the elastic band is attached to a portion of the puppet on a second side of the puppet thereby forming a closed loop.

2. The cast cover of claim 1 wherein the first end of an elastic band is attached to a first appendage on a first side of the puppet and the second end of the elastic band is attached to a second appendage on a second side of the puppet.

3. The cast cover of claim 2 wherein the puppet is a stuffed toy having a body and at least one set of appendages.

4. A cast cover comprising:
    an elongated tubular leg portion comprising a material configured to form a first elongated opening wherein the material forming the elongated tubular leg portion completely surrounds the first elongated opening; and
    a foot portion extending from the leg portion wherein the foot portion comprises material configured to form a second elongated opening wherein the material forming the foot portion completely surrounds the second elongated opening wherein the material forming the foot portion comprises a top portion, a bottom portion, a first side portion extending from the top portion to the bottom portion on a first side of the foot portion, and a second side portion extending from the top portion to the bottom portion on a second side of the foot portion wherein the top portion comprises a first piece of material and second piece of material wherein the first piece of material overlaps the second piece of material and is detachable from the second piece of material along an edge of the first piece of material extending in the direction of the second elongated opening thereby forming a flap,
    wherein the leg portion and foot portion are configured to receive a cast or brace therein.

5. The cast cover of claim 4 wherein the foot portion further comprises one or more non-slip pads on the bottom portion of the material forming the foot portion.

6. The cast cover of claim 4 wherein the edge of the first piece of material of the top portion of the material forming the foot portion extends to a portion on the bottom portion of the material forming the foot portion.

7. A cast cover comprising:
    an elongated tubular portion comprising a material configured to form a first elongated opening wherein the material forming the elongated tubular leg portion completely surrounds the first elongated opening wherein the elongated tubular portion comprises a first end and a second end wherein the first end includes a first opening configured to receive a cast or brace therein; and
    a hand portion extending from the second end of the elongated tubular portion wherein the hand portion comprises a material configured to form a second elongated opening wherein the material forming the hand portion completely surrounds the second elongated opening wherein the hand portion comprises a distal end comprising a second and third opening formed by the material forming the hand portion wherein the second opening is configured to receive one or more fingers of a wearer and the third opening is configured to receive the thumb of the wearer; and
    a thumb strap wherein the thumb strap comprises an elongated piece of material extending from the cast cover on a side opposite the third opening wherein the thumb strap further comprises fastening means thereon for securing the distal end of the thumb strap to the cast cover.

* * * * *